United States Patent
Martin et al.

(12) 
(10) Patent No.: US 6,540,706 B1
(45) Date of Patent: Apr. 1, 2003

(54) SPLINT PRODUCT WITH A MOISTURE-IMPERVIOUS LAYER THAT IS AN INTEGRAL PART OF THE PRODUCT

(75) Inventors: James C. Martin, Baldwin City, KS (US); Larry R. DeCamp, Lawrence, KS (US); Patricia A. Goulette Monroe, Lawrence, KS (US); Randall S. Kilburn, Lawrence, KS (US)

(73) Assignee: M-Pact Worldwide L.L.C., Eudora, KS (US)

( * ) Notice: Subject to any disclaimer, the term of this patent is extended or adjusted under 35 U.S.C. 154(b) by 0 days.

(21) Appl. No.: 09/524,866

(22) Filed: Mar. 14, 2000

(51) Int. Cl.[7] .................................................. A61F 5/00
(52) U.S. Cl. ............................................. 602/6; 602/8
(58) Field of Search ............................. 602/5–9, 60, 63

(56) References Cited

U.S. PATENT DOCUMENTS

| | | |
|---|---|---|
| 4,193,395 A | 3/1980 | Gruber |
| 4,235,228 A | 11/1980 | Gaylor, Jr. et al. |
| 4,344,423 A | 8/1982 | Evans et al. |
| 4,433,680 A | 2/1984 | Yoon |
| 4,442,833 A | 4/1984 | Dahlen et al. |
| 4,454,874 A | 6/1984 | Monnier |
| 4,628,917 A | 12/1986 | Campagna, Jr. et al. |
| 4,770,299 A | 9/1988 | Parker |
| 4,869,046 A | 9/1989 | Parker |
| 4,888,225 A | 12/1989 | Sandvig et al. |
| 4,899,738 A * | 2/1990 | Parker ........................... 602/8 |
| 5,003,970 A | 4/1991 | Parker et al. |
| 5,027,803 A * | 7/1991 | Scholz ........................... 602/8 |
| 5,171,208 A | 12/1992 | Edenbaum et al. |
| 5,176,621 A | 1/1993 | Schulz |
| 5,284,468 A * | 2/1994 | Nelson ........................... 602/8 |
| 5,318,504 A | 6/1994 | Edenbaum et al. |
| 5,520,621 A | 5/1996 | Edenbaum et al. |
| 5,607,387 A * | 3/1997 | Martin ........................... 602/8 |

* cited by examiner

Primary Examiner—Michael A. Brown
(74) Attorney, Agent, or Firm—Stinson Morrison Hecker LLP

(57) ABSTRACT

A splint product for forming a hard structure about a body portion is provided. The splint product includes a unitary assembly of moisture-impervious outer and inner layers with an outer substrate layer, a resin impregnated substrate that hardens when exposed to moisture, and an inner substrate layer disposed between these moisture-impervious layers. Padding is adhered to the moisture-impervious inner layer opposite said resin impregnated substrate so that the padding is in contact with a patient's skin. Another aspect of the present invention is a method for activating the splint product by exposing the outer substrate layer and/or the resin impregnated substrate to moisture. This may be done by removing the moisture-impervious outer layer and spraying water on the outer substrate layer or by holding the moisture-impervious inner and outer layers together to form a pouch and pouring water into this pouch. Still another embodiment of the present invention is a method of resealing the packaging of the splint product of the present invention using a clamp.

31 Claims, 1 Drawing Sheet

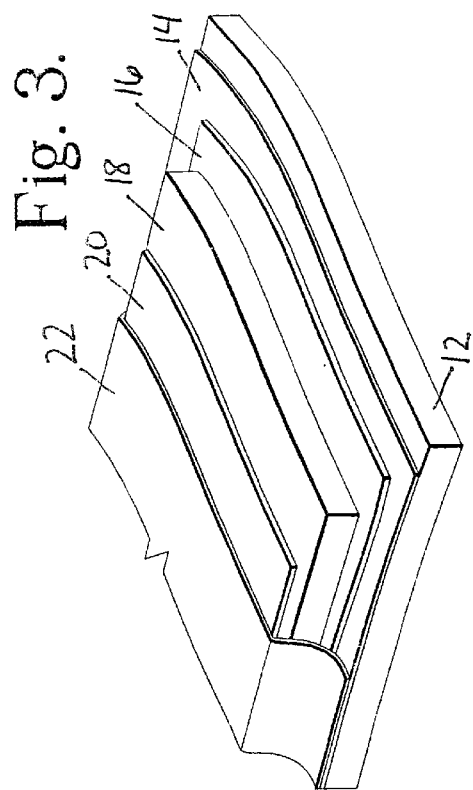
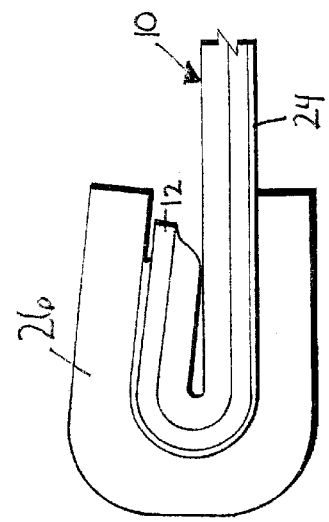
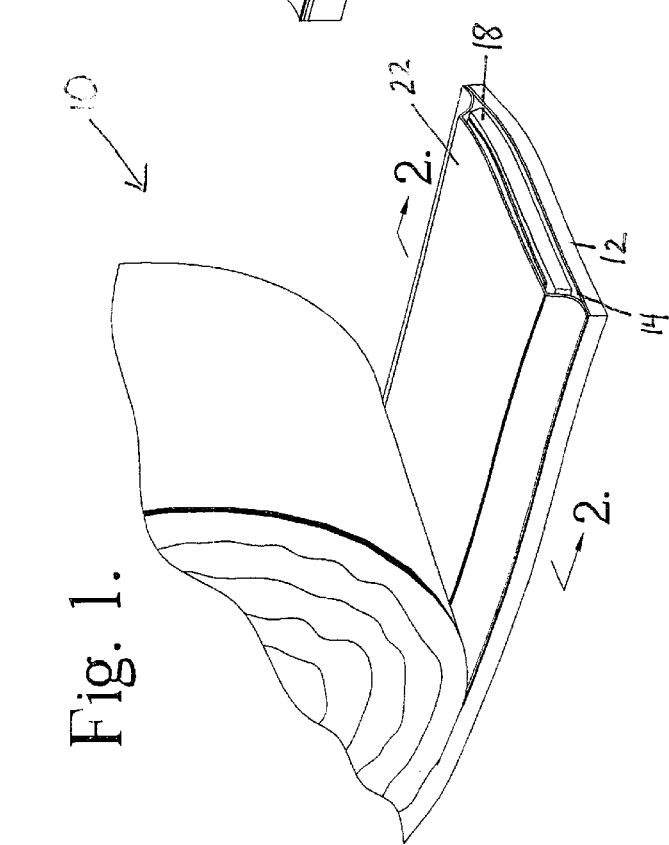
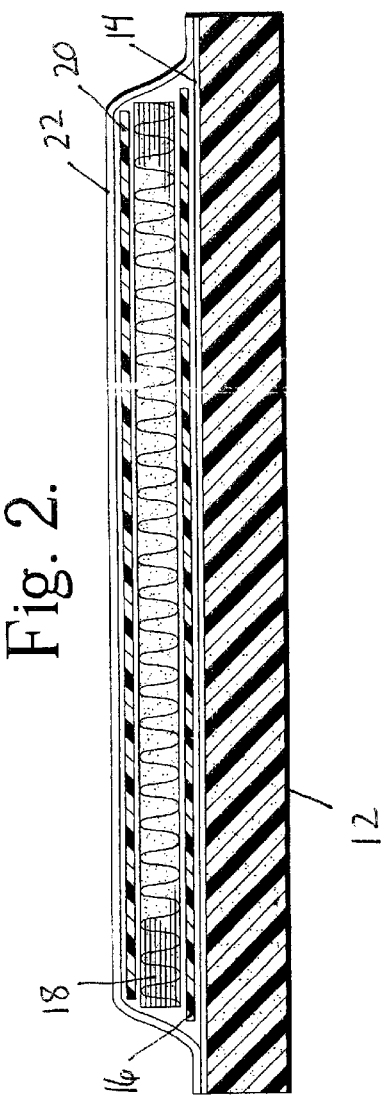

SPLINT PRODUCT WITH A MOISTURE-IMPERVIOUS LAYER THAT IS AN INTEGRAL PART OF THE PRODUCT

STATEMENT REGARDING FEDERALLY SPONSORED RESEARCH OR DEVELOPMENT

Not Applicable.

CROSS-REFERENCE TO RELATED APPLICATIONS

Not Applicable.

BACKGROUND OF THE INVENTION

The present invention relates to an orthopedic splint product. More particularly, the splint product of the present invention includes a moisture-impervious layer that functions as both packaging for the splint product and as a moisture/vapor barrier once the splint product is on the patient.

Casts and splints have traditionally been made by coating or impregnating a substrate, usually fabric, such as gauze, mesh or fiberglass, with a dry casting material such as plaster of Paris. The coated substrate is then dipped in water or some other liquid-activating substance to initiate the setting of the casting material. Following this, the coated substrate is squeezed to remove excess water, placed on the appropriate part of the patient, wrapped with an elastic bandage, and allowed to cure.

One disadvantage with these traditional casts and splints is that initiating setting is often messy and time consuming. Still further, the activating process requires multiple supplies and considerable skill. Usually the person applying a traditional cast or splint wears gloves and protective clothing, and often a protective layer of material is placed on the patient to protect the skin (see, for example, U.S. Pat. No. 4,193,395, which refers to covering the body part receiving the splint with a stockinette). The traditional casts and splints can be even messier if colored resins and/or substrates are used.

Other casting materials have been proposed that enclose the casting material in sleeves or coverings so that direct contact with the casting material is not necessary. Examples of such casting devices are described in U.S. Pat. Nos. 4,235,228, 4,442,833, 4,454,874, 4,628,917, 4,770,299, 4,869,046 and 4,899,738. However, these devices still have the disadvantage of requiring the device to be submerged in water and then wrung out before being applied to the appropriate body part of the patient. This method of application results in a wet layer of material being put in direct contact with a patient's skin. This may be uncomfortable and irritating and can, in time, cause maceration and sloughing of the skin. Another disadvantage with these casting materials is that, like traditional casts, they require submergence in a bucket of water or running water to initiate setting, and this limits their portability.

Other devices have been proposed that include a totally moisture impermeable layer for placement next to the skin, as discussed in U.S. Pat. No. 4,454,874. While this type of splint or cast may prevent moisture from the casting material from contacting the skin, the disadvantage with such a device is that moisture that is normally released from the skin becomes trapped. This moisture builds up under the impermeable layer and may cause tissue damage and/or odor.

It has further been suggested to apply a separate dry pad to a patient or adhere this dry pad to a casting device after it is wetted such as, for example, as described in U.S. Pat. Nos. 4,193,395 and 4,628,917. One disadvantage with such devices is that they are not unitary. If an adhesive is used to hold the components together, it usually does not hold well in a moisture environment. Still further, the separate dry pad may restrict the respiration of vapor.

Devices have also been proposed that use hydrophobic material on the patient contact side, as discussed in U.S. Pat. Nos. 4,770,299, 4,869,046 and 4,899,738. However, these devices still require immersing the device in water for activation of the resin. The immersion and squeezing of the device results in water being trapped or retained in the spaces of the hydrophobic material causing a wet surface to be presented to a patient. Still further, such devices may trap moisture next to the patient's skin.

Still other devices are described in U.S. Pat. Nos. 5,171,208 and 5,318,504. These devices provide a layer of water-impermeable, water vapor-permeable film on the side of the device in contact with the patient's skin. The film is placed next to the patient's skin to release trapped moisture while the cast or splint is in place on the patient. Still further, the film prevents water or other liquid from penetrating through the device to contact the patient's skin while the device is curing or if the device is exposed to liquid. These devices can be made without the need to be fully immersed in liquid when made with a preformed liquid-containing pouch formed of water-permeable, spun-bonded polypropylene. One disadvantage with these devices is that water cannot be removed from these devices once they are activated. Excess water remaining in the product could cause mold to grow. Still further, another disadvantage with these devices is that padding is exposed to moisture in these devices. Furthermore, these devices are stored in metallic packaging, which is separate from the product.

Another disadvantage with casting or splint products that are currently available is that those that use a low viscosity resin, when formulated to give a proper set time, typically result in unacceptably high temperature exothermic reactions, which can result in burning the patient. High viscosity resins, on the other hand, typically require complicated techniques for application, such as solvent coating the resin onto the fabric or substrate. Further, the fabrics or scrim materials used in such splints have typically been relatively inextensible in order to provide sufficient strength for the resulting splint. This results in a splinting material that has poor extensibility and that does not conform well to the body part to which it is applied.

As mentioned previously, a common disadvantage with a number of the splinting materials in the prior art is that they do not exhibit sufficient water vapor permeability, and skin maceration therefore can result from their use. Also, many of the splinting products currently available must be removed before a patient is x-rayed. Still further, many of the splinting products currently available are comprised of fiberglass, and health risks have been associated with the use of fiberglass. Even further, many of the splinting products currently available are disposed in landfills once they are removed.

To overcome the deficiencies found with conventional splinting and casting products, a splinting device that provides initial stiffness for quick immobilization while allowing time for molding the splinting material to the body is needed. Still further, this device should minimize the effects of exothermic reactions during its set-time and should discourage conditions that cause skin maceration while the splint is in place. A splint product of the present invention should also avoid the use of fiberglass to prevent health risks and should be made of environmentally friendly components.

SUMMARY OF THE INVENTION

It is an object of the present invention to provide a splint product that incorporates faster setting and slower setting substrate layers to provide fast green strength in the outer layers and conformability and a lower exotherm near a patient's skin.

It is a further object of this invention to provide a splint product having a moisture barrier layer near the skin and a padding layer against the skin designed to wick moisture away from the skin so as to provide greater patient comfort.

Another object of the present invention is to provide a splint product that can be activated using a variety of wetting techniques so as to increase the utility of the device.

Another object of the present invention is to provide a splint product that is radiolucent so that it does not have to be removed to monitor a patient's recovery.

A further object of the present invention is to provide a splint product that can be disposed of by burning it so that it is considered environmentally friendly.

According to the present invention, the foregoing and other objects are achieved by a splint product that includes moisture-impervious outer and inner layers with an outer substrate layer, a resin impregnated substrate, and an inner substrate layer disposed between these moisture-impervious layers. Padding is adhered under the moisture-impervious inner layer opposite the resin impregnated substrate so that the padding is in contact with a patient's skin. The term "splint product" includes splinting materials and/or casting materials. Another aspect of the present invention is a method of activating this splint product by exposing the outer substrate layer to moisture. This may be done by removing the moisture-impervious outer layer and spraying water on the outer substrate layer or by holding the moisture-impervious inner and outer layers together to form a pouch and pouring water into this pouch. Still another embodiment of the present invention is a method of resealing the packaging of the splint product of the present invention using a clamp.

Additional objects, advantages, and novel features of the invention will be set forth in the description that follows and in part will become apparent to those skilled in the art upon examination of the following, or may be learned by practice of the invention.

BRIEF DESCRIPTION OF THE DRAWINGS

In the accompanying drawings, which form a part of the specification and are to be read in conjunction therewith, and in which like reference numerals are used to indicate like parts in the various views:

FIG. 1 is the splint product of the present invention shown packaged in a continuous roll;

FIG. 2 is a cross sectional view of the splint product shown in FIG. 1 taken along line 2—2;

FIG. 3 is a perspective view of the splint product of the present invention with parts broken away to show details of construction; and FIG. 4 is a cross-sectional view of the splint product and clamp of the present invention.

DETAILED DESCRIPTION OF THE PREFERRED EMBODIMENT

Referring to FIG. 1, a splint product embodying the principals of the present invention is shown and is broadly designated by the reference numeral 10. As shown in more detail in FIGS. 2 and 3, this splint product 10 includes padding 12, which is placed next to a patient's skin. Padding 12 is adhered to moisture-impervious inner layer 14. An inner substrate layer 16 is adjacent moisture-impervious inner layer 14 on the opposite side of padding 12. A resin impregnated substrate 18 is disposed on the outer side of inner substrate layer 16. An outer substrate layer 20 is disposed on the outer side of resin impregnated substrate 18. A moisture-impervious outer layer 22 is then disposed on the outer side of outer substrate layer 20.

Moisture-impervious outer layer 22 is joined at its peripheral edge with the peripheral edge of moisture-impervious inner layer 14, as shown in FIG. 3. Outer substrate layer 20, resin impregnated substrate 18, and inner substrate layer 16 are enclosed between the moisture-impervious outer and inner layers, 22 and 14. Layers 16, 18, and 20 are sized so that the peripheral edges of the moisture-impervious layers extend beyond the peripheral edges of these inner layers. As shown in FIG. 4, when splint product 10 is repackaged, the ends of moisture-impervious inner and outer layers 14 and 22 are sealed together using template 24 and clamp 26.

Padding 12 is designed to wick moisture expelled by the patient's skin to the outer edge of the padding where it can evaporate so that moisture generated within the skin will not stay near the skin and cause skin maceration. It allows the skin to transpire moisture. Examples of materials that padding 12 can be made of include, but are not limited to, synthetic material, such as polyester or polypropylene, or foamed polymers, such as open-celled foam. Open-celled foam can be made from polyurethane. Preferably, padding 12 is made of polypropylene. Most preferably, padding 12 is Medical Polypropylene #NW 700, having 7.5 ounces per square yard and nominal 3 denier, obtained from Rogers Corporation of Rogers, Conn. It may be treated with an antimicrobial agent such as Tween 20 from ICI America's Inc. of Wilmington, Del. Preferably, padding 12 is adhesively secured to moisture-impervious inner layer 14. However, in an alternate embodiment of the present invention, padding need not be a part of splint product 10, and instead, a separate piece of padding could be placed on a portion of a patient's skin before the splint product is molded to that portion. In either embodiment, the padding does not get wet when the splint product is activated.

Moisture-impervious inner layer 14 has a low moisture vapor transmission rate (MVTR). About 0.02 grams or less of moisture are able to penetrate it over 24 hours per 100 square inches. Preferably, moisture-impervious inner layer 14 is made of a material that adheres to both padding 12 and inner substrate layer 16. It provides a moisture and thermal barrier between the padding and the outer layers of the splint product. It should be translucent so as to allow the splint product to be radiolucent. Preferably, moisture-impervious inner layer 14 is comprised of a carrier film, a moisture barrier film laminated thereto, and a heat sealable coating. The carrier film may be, but is not limited to, polyester, nylon, or polypropylene. Moisture from outside the splint or vapor from the curing of the resin impregnated substrate is prevented from penetrating through this moisture-impervious layer 14 to a patient's skin. It further protects a patient from exposure to any liquid that may be spilled on the splint product. It also protects the skin from heat caused by the exothermic reactions of the resin setting. Still further, it prevents resin from touching padding 12.

Most preferably, moisture-impervious inner layer 14 is GLAE polyester film of a 2.8 mm thickness with a 2.3 mm low density polyethylene peelable film laminate thereon and is obtained from Genesis Converting of Itasca, Ill. Moisture-impervious inner layer 14 serves as both a packaging layer so as to shield layers 16, 18, and 20 from moisture before the splint product is used, and also it serves as a moisture and thermal barrier once the splint product is in place to keep moisture and heat from the skin. It also provides support and stiffness to splint product 10.

Inner substrate layer 16 may be impregnated with a resin, such as polyurethane. Inner substrate layer 16 is comprised of a textile material such as woven or non-woven polyester or fiberglass. Preferably, inner substrate layer 16 is comprised of non-woven polyester. Most preferably, inner substrate layer 16 is obtained from Tietex International, Ltd. of Spartanburg, S.C. This layer is optional and is not included in the most preferred embodiment of the present invention.

The substrate of resin impregnated substrate 18 can be made of man-made or natural fibers. It should be made of a material that is moldable. Examples of suitable materials for this substrate include, but are not limited to, polyester, fiberglass, kevlar, and aerospace fabric. Preferably, the substrate is not fiberglass and instead is made of a burnable material. Examples of materials that the resin may be comprised of include, but are not limited to, functional pre-polymer isocyanate and polyurethane. Most preferably, resin impregnated substrate 18 is polyester woven fabric coated with polyurethane resin with the polyurethane resin being about 51% of the total weight of the product. It may be obtained from Con Ap, Inc. of Olean, N.Y. Usually, between about 1 and 15 layers of resin impregnated substrate are used in making the splint product. Preferably, between about 5 and 10 layers of resin impregnated substrate are used. Most preferably, about 8 layers of this resin impregnated substrate are used to a obtain a splint product of a desired strength. Substrate impregnated resin 18, in most instances, has a greater thickness than both outer substrate layer 20 and inner substrate layer 16.

Outer substrate layer 20 is a release liner. It can be made of woven or non-woven polyester or fiberglass. This layer may be treated with a surfactant. Preferably, outer substrate layer 20 is comprised of non-woven polyester. Most preferably, outer substrate layer 20 is Medical Polypropylene #NW 715, having 2.5 ounces per square yard, obtained from Rogers Corporation of Rogers, Conn. Most preferably, this layer is coated with surfactant #193, obtained from Dow Corning Corporation of Auburn, Mich., to improve its water absorption. This layer allows moisture-impervious outer layer 22 to be easily released therefrom and provides good transmission of water to resin impregnated substrate 18 once activation begins. Still further, it prevents the resin in resin impregnated substrate 18 from sticking to moisture-impervious outer layer 22 or from sticking to the patient or to the person applying the splint product. This outer substrate layer 20 is optional but preferably is included for the reasons described above. If outer substrate layer 20 is included in splint product 10, it can be from 1 to 3 layers. Preferably, it is one layer.

Moisture-impervious outer layer 22 has a low moisture vapor transmission rate (MVTR). About 0.02 grams or less of moisture are able to penetrate it over 24 hours per 100 square inches. Moisture-impervious outer layer 22 can be made of the same material as moisture-impervious inner layer 14. However, it need not be translucent because in most instances it does not remain a part of the splint product once the splint product is put on a patient. Most preferably, moisture-impervious outer layer 22 is white nylon foil obtained from Genesis Converting of Itasca, Ill. under the tradename #PF360W in a thickness of 4.5 mil. Moisture-impervious outer layer 22 may have printed indicia thereon. This printed indicia may include instructions for activating and using splint product 10.

Another aspect of the present invention is a method of activating splint product 10 by exposing resin impregnated substrate 18 to moisture. In one embodiment, moisture-impervious outer layer 22 in combination with moisture-impervious inner layer 14 may be used as a reservoir or pouch for wetting outer substrate layer 20, resin impregnated substrate 18, and inner substrate layer 16. In this embodiment, one end of moisture-impervious inner layer 14 and one end of moisture-impervious outer layer 22 are held closed and the sides of these layers are removably joined at their peripheral edges to form a pouch. Water is poured into the pouch to activate layers 16, 18, and 20. The water is then poured out and moisture-impervious outer layer 22 is removed. Alternatively, in another embodiment of the invention, moisture-impervious outer layer 22 can be removed before the layers 16, 18, and 20 are moisture activated. In this embodiment, moisture-impervious outer layer 22 is peeled away from moisture-impervious inner layer 14. Following this, water is sprayed on outer substrate layer 20 (unless it is not included in splint product 10 and then the water is sprayed on resin impregnated substrate 18). A spray of water combined with water present in the atmosphere is all that is required to begin the setting process. The amount of water used is proportional to the setting time of the splint product. The more water used, the quicker setting time. Also, the hotter the water used, the quicker setting time. For either of these embodiments, by varying the amount of water used and the water's temperature, the technician has more control over the set time of the splint, allowing for a faster set time if initial strength is most important or a slower set time if more time is needed for molding the splint. It is especially easy to control amount of water used and therefore the set time when using the spraying method. For example, the set time can be modified to provide more time for placement of larger splints, such as those needed for injuries involving the lower extremities. In either of these embodiments, padding 12 is never exposed to water.

After splint product 10 is put on a patient, it is wrapped with an elastic bandage. Preferably, splint product 10 includes outer substrate layer 20 so that this layer is adjacent to the elastic bandage rather than the resin impregnated substrate, which may not be fully cured and therefore somewhat sticky, being next to the elastic bandage.

Preferably, outer substrate layer 20 is treated with or impregnated with a surfactant that is designed to accelerate water interaction with resin impregnated substrate 18. Still further, preferably, resin impregnated substrate 18 is designed to be faster setting than inner substrate layer 16. This allows the exterior of the splint product to harden initially for strength while the interior of the splint product has time to conform to the patient.

Still further, preferably, the outer layers of resin impregnated substrate 18 set quicker than the inner layers. For example, when resin impregnated substrate has 8 layers, the top 2 or 3 layers will set quicker than the 4 or 5 layers closest to the patient's skin. This is accomplished by using polyurethane resins of different compositions to provide different cure times.

The setting time of the layers closer to the patient's skin is within the range of approximately 3 to 6 minutes following activation with room temperature water, and the setting time of the layers closer to the atmosphere is within the range of approximately 2 to 4 minutes following activation. The temperatures reached within the outer substrate layer and the outer layers of the resin impregnated substrate fall within the range of approximately 95° to 115° F. The temperatures within the inner substrate layer and the inner layers of the resin impregnated substrate fall with the range of 80° to 90° F.

The different layers of the splinting material each provide a unique function within splint product 10 and have been designed to provide a resilient yet strong splint. The strength of the product must be increased with the size of the product being used. The strength of the splinting device is obtained from the textile materials rather than from the resins so as to provide a lighter weight and lower profile splint product. This product is 0.320 inches thick whereas conventional products are 0.530 inches thick or more.

The splint product of the present invention may be provided in a continuous roll or may be pre-cut into pieces of a predetermined size. As discussed above, it is thinner than products in the prior art. It can be made in a number of widths. Common widths include 2 to 3 inch wide splint product for use on arms and 4 to 6 inch wide splint product for use on legs.

If this product is in a continuous roll, a desired length of splint product is pulled off the roll and cut off. It is easier to cut than splints made from fiberglass substrates. The preferred splint product of the present invention also does not have the spiculite problem (sharp glass fibers resulting when cuts are made) of fiberglass when it is cut off. The continuous roll is in a resealable package. The outer substrate layer 20, resin impregnated substrate 18, and inner substrate layer 16 are rolled back from the cut line so that the moisture-impervious inner and outer layers 14 and 22 can be clamped together. Some of the sticky resin from the resin impregnated substrate will have touched the inner surfaces of moisture-impervious inner and outer layers 14 and 22 and further helps hold these layers together. Preferably, the continuous roll package will have a scored folding corrugated template 24 attached thereto. This template 24 can be made of cardboard or other flexible material. This template is designed to precisely measure and aid in the folding of layers 14 and 22 together. Preferably, these layers are folded using the template 24, and then the layers and template are clamped together using clamp 26.

The splint product of the present invention can be radiolucent so that X-rays can be taken without having to remove it. For the splint product to be radiolucent, the moisture-impervious inner layer must not be made of foil.

The splint product of the present invention does not require running water for its activation. In fact, it can be activated using fairly small quantities of water, 0.4 cc/square inch of splint product. Therefore, the splint product of the present invention is fairly portable.

Preferably, the splint product of the present invention contains no fiberglass and thus avoids the health risks associated with using fiberglass. In addition, preferably, the materials used in making the present invention are 100% incineratable so as to aid in the disposal of the splint product once it has been removed from the patient. Waste is further reduced in the splint product of the present invention by integrating the packaging into the product. By using moisture-impervious inner layer 14 as both packaging and as a moisture vapor barrier once the product is on the patient, it reduces the amount of packaging for this product.

Still another aspect of the present invention is a method of making a splint product comprising providing padding, placing a moisture-impervious inner layer on the padding, placing a resin impregnated substrate on the moisture-impervious inner layer, placing an outer substrate layer on the resin impregnated substrate, and placing a moisture-impervious outer layer on the outer substrate layer. The peripheral edges of the moisture-impervious inner and outer layers are joined so as to surround layers 16, 18, and 20.

From the foregoing, it will be seen that this invention is one well-adapted to attain all the ends and objects hereinabove set forth together with other advantages which are obvious and inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative not a limiting sense.

We claim:

1. A splint product for forming a hard structure about a body portion, comprising a unitary assembly of:
   a moisture-impervious inner layer having a peripheral edge;
   a moisture-impervious outer layer having a peripheral edge removably joined with said peripheral edge of said moisture-impervious inner layer; and
   a substrate impregnated with a resin that hardens when exposed to moisture said substrate being disposed between said moisture-impervious inner and outer layers.

2. The splint product of claim 1, further comprising:
   an outer substrate layer disposed between said resin impregnated substrate and said moisture-impervious outer layer.

3. The splint product of claim 2, wherein said outer substrate layer is comprised of at least one layer of woven or non-woven polyester.

4. The splint product of claim 2, wherein said outer substrate layer is treated with a surfactant.

5. The splint product of claim 2, further comprising:
   an inner substrate layer disposed between said resin impregnated substrate and said moisture-impervious inner layer.

6. The splint product of claim 5, wherein said inner substrate layer is comprised of woven or non-woven polyester.

7. The splint product of claim 5, wherein said inner substrate layer is impregnated with a resin.

8. The splint product of claim 1, further comprising:
   padding adhered to said moisture-impervious inner layer opposite said resin impregnated substrate.

9. The splint product of claim 8, wherein said padding is able to wick moisture away from a person's skin.

10. The splint product of claim 9, wherein said padding is comprised of non-woven polyester or open-celled foam.

11. The splint product of claim 1, wherein said substrate is impregnated with a water-activated polyurethane resin.

12. The splint product of claim 11, wherein said substrate is comprised of woven or non-woven polyester.

13. The splint product of claim 12, wherein said resin impregnated substrate is comprised of between about 1 and 15 layers of polyurethane resin impregnated woven polyester.

14. The splint product of claim 1, wherein said moisture-impervious inner layer and said moisture-impervious outer layer shield said resin impregnated substrate from exposure to moisture in the atmosphere.

15. The splint product of claim 1, wherein said moisture-impervious outer layer and said moisture-impervious inner layer have a moisture vapor transmission rate of about 0.2 grams or less of moisture penetration over 24 hours per 100 square inches.

16. The splint product of claim 15, wherein said moisture-impervious inner layer is comprised of a carrier film, a moisture barrier film laminated to said carrier film, and a heat sealable coating.

17. The splint product of claim 15, wherein said moisture-impervious outer layer has printed indicia thereon.

18. The splint product of claim 1, wherein said splint product is radiolucent.

19. The splint product of claim 2, wherein said outer substrate layer is able to set faster than said resin impregnated substrate.

20. The splint product of claim 19, wherein the amount of heat generated from said resin setting decreases closer to a person's skin.

21. The splint product of claim 5, wherein said resin impregnated substrate is able to set faster than said inner substrate layer.

22. The splint product of claim 1, wherein the setting speed of said splint product increases in proportion to the amount of water to which said splint product is exposed.

23. The splint product of claim 1, wherein said splint product is stored in a continuous roll.

24. The splint product of claim 1, wherein said splint product is incineratable.

25. A method of making a splint product, comprising:
   providing padding;
   placing a moisture-impervious inner layer having a peripheral edge on said padding;
   placing a resin impregnated substrate on said moisture-impervious inner layer;
   placing an outer substrate layer on said resin impregnated substrate; and
   placing a moisture-impervious outer layer having a peripheral edge on said outer substrate layer.

26. The method of claim 25, further comprising:
   joining said peripheral edge of said moisture-impervious inner layer with said peripheral edge of said moisture-impervious outer layer.

27. A method of activating a splint product comprising a unitary assembly of a moisture-impervious inner layer having a peripheral edge, a moisture-impervious outer layer having a peripheral edge removably joined with said peripheral edge of said moisture-impervious inner layer, and a substrate impregnated with a resin that hardens when exposed to moisture said substrate being disposed between said moisture-impervious inner and outer layers, comprising:
   exposing said resin impregnated substrate to moisture.

28. The method of claim 27, wherein said exposing step includes holding said moisture-impervious inner and outer layers together to form a pouch and pouring water in said pouch.

29. The method of claim 27, wherein said exposing step includes removing said moisture-impervious outer layer from said splint product and spraying water on said splint product so as to moisten said resin impregnated substrate.

30. A splint product for forming a hard structure about a body portion, comprising a unitary assembly of:
   a moisture-impervious inner layer having a peripheral edge;
   a moisture-impervious outer layer having a peripheral edge removably joined with said peripheral edge of said moisture-impervious inner layer;
   a substrate impregnated with a resin that hardens when exposed to moisture said substrate being disposed between said moisture-impervious inner and outer layers;
   an outer substrate layer disposed between said resin impregnated substrate and said moisture-impervious outer layer; and
   padding adhered to said moisture-impervious inner layer opposite said resin impregnated substrate.

31. A method of resealing unused splint product comprising a unitary assembly of a moisture-impervious inner layer having a peripheral edge, a moisture-impervious outer layer having a peripheral edge removably joined with said peripheral edge of said moisture-impervious inner layer, and a substrate impregnated with a resin that hardens when exposed to moisture said substrate being disposed between said moisture-impervious inner and outer layers, said method comprising:
   providing a clamp;
   providing a template;
   rolling said resin impregnated substrate away from said moisture-impervious inner and outer layers;
   pressing one end of said moisture-impervious outer layer against one end of said moisture-impervious inner layer;
   aligning said moisture-impervious inner and outer layers with said template;
   folding said moisture-impervious inner and outer layers and said template; and
   placing said clamp over said folded layers and said template.

* * * * *